(12) United States Patent
Burke et al.

(10) Patent No.: US 6,323,204 B1
(45) Date of Patent: *Nov. 27, 2001

(54) METHODS FOR USING (2-IMIDAZOLIN-2-YLAMINO) QUINOXALINE DERIVATIVES

(75) Inventors: James A. Burke, Santa Ana; Michael E. Garst, Newport Beach; Larry A. Wheeler, Irvine, all of CA (US)

(73) Assignee: Allergan, Waco, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/222,844

(22) Filed: Dec. 30, 1998

Related U.S. Application Data

(63) Continuation-in-part of application No. 09/012,517, filed on Jan. 23, 1998, now abandoned, which is a division of application No. 08/636,740, filed on Apr. 19, 1996, now Pat. No. 5,756,503, which is a division of application No. 08/458,949, filed on Jun. 2, 1995, now Pat. No. 5,587,376, which is a division of application No. 08/390,265, filed on Feb. 15, 1995, now Pat. No. 5,561,132, which is a continuation of application No. 08/135,716, filed on Oct. 13, 1993, now abandoned.

(51) Int. Cl.[7] .................................................. A61K 31/495
(52) U.S. Cl. ............................................................ 514/249
(58) Field of Search .................................................. 514/249

(56) References Cited

U.S. PATENT DOCUMENTS

| | | | |
|---|---|---|---|
| 3,890,319 | * 6/1975 | Daneilewicz et al. | 260/250 Q |
| 4,188,393 | 2/1980 | Neuman | 424/258 |
| 4,656,291 | 4/1987 | Maryanoff et al. | 544/315 |
| 5,021,416 | 6/1991 | Gluchowski | 514/249 |
| 5,034,406 | 7/1991 | Gluchowski | 514/377 |
| 5,077,292 | 12/1991 | Gluchowski | 514/249 |
| 5,112,822 | 5/1992 | Gluchowski | 514/249 |
| 5,130,441 | 7/1992 | Gluchowski | 548/351 |
| 5,198,442 | 3/1993 | Gluchowski | 514/249 |
| 5,204,347 | 4/1993 | Gluchowski | 514/249 |
| 5,231,096 | 7/1993 | Gluchowski | 514/249 |
| 5,237,072 | 8/1993 | Gluchowski | 548/323.5 |
| 5,756,503 | * 5/1998 | Burke et al. | 514/249 |

FOREIGN PATENT DOCUMENTS

| | | |
|---|---|---|
| 2309160 | 9/1973 | (DE) . |
| 2538620 | 8/1975 | (DE) . |
| 0422878 | 4/1991 | (EP) . |
| 0426390 | 5/1991 | (EP) . |
| 1463520 | 2/1977 | (GB) . |
| 11851 | 12/1989 | (WO) . |
| 9313771 | 7/1993 | (WO) . |
| 9510280 | 4/1995 | (WO) . |

OTHER PUBLICATIONS

Williams et al, J. Auton. Pharmacol., 10 (4):247, 8/90.
Fielding, Midicinal Research Reviews, vol. 1, No. 1, pp. 97–123, 1981.
Isom et al, The Journal of Biological Chemistry, vol. 262, No. 14, pp. 6750–6757, 5/87.
Timmermans et al, Eur. J. Med. Chem., vol. 4, pp. 323–329, 1980.
Langer et al, Journal of Cardiovascular Pharm., vol. 7, Supp. 8 (S1–S8) (1985).
Nielsen et al, Br. J. Pharmacol, 97 (834), 1989.
B. Bloor, Seminars in Anesthesia, vol. VII, No. 3, pp. 170–177, Sep. 1988.
Sato et al, Science, vol. 251, pp. 1608–1610, Mar. 1991.
Gellai et al, The Journal of Pharamacology & Exp. Therap., 240(3), pp. 723–728, 1987.
Bloor et al, Anesthesia & Analgesia, vol. 61, No. 9, 741–745, 9/82.
Van Zwieten et al, Advances in Drug Research, vol. 13, 209–254, 1984.
Dharmsathaphorn, Gastroenterology, 91(3), 769–70, 1986.
Mittag, Annals of Ophthalmology, 201–2, Mar. 1983.
Jumblatt et al, Current Eye Research, vol. 6, pp. 767–777, 1987.
Burke et al, Current Eye Research, vol. 5, pp. 665–676, 1986.
Fondacaro et al, American Society for Pharmacology, vol. 247, (1987) pp 481–486.
Bendele et al, Pharmacol, 82, pp. 152, Aug. 1991.

(List continued on next page.)

*Primary Examiner*—Gary Geist
*Assistant Examiner*—Everett White
(74) *Attorney, Agent, or Firm*—Stout, Uxa, Buyan & Mullins, LLP; Frank J. Uxa

(57) ABSTRACT

A method of treating a mammal comprises administering to a mammal an effective amount to provide a desired therapeutic effect in the mammal of a compound selected from the group consisting of those having the formula:

and pharmaceutically acceptable acid addition salts thereof and mixtures thereof, wherein $R_1$ and $R_2$ each is selected from the group consisting of alkyl radicals containing 1 to 4 carbon atoms and alkoxy radicals containing 1 to 4 carbon atoms, the 2-imidazolin-2-ylamino group may be in any of the 5-, 6-, 7- or 8-positions of the quinoxaline nucleus, and $R_3$, $R_4$ and $R_5$ each is located in one of the remaining 5-, 6-, 7- or 8-positions of the quinoxaline nucleus and is independently selected from the group consisting of Cl, Br, H and alkyl radicals containing 1 to 3 carbon atoms. Such compounds, when administered to a mammal, provide desired therapeutic effects, such as reduction in peripheral pain.

17 Claims, No Drawings

OTHER PUBLICATIONS

Goodman & Gilman et al, The Pharmacological Basis of Therapeutics, 7TH Ed., Ch. 8, pp. 174–179, 1985.

Berridge et al, Br. J. Pharmac., 88(2), 345–354, 1986.

Thaina et al, J. Autonomic Pharamacology, 13(2), 95–176, 1993.

Hayes et al, Neuropharmacology, 25(4), 391–396, 1986.

Gellai et al, Am. Physio. Soc., F317–323, 1988.

Colpaert, F.C., Drug Development Research, 7:209–220, 1986.

Pharmsathaphorn et al, Gastroenterology, 86(1), 120–128, 1984.

Contiello et al, J. Biol. Chem., 264 (27), pp. 16000–16007, 1989.

Thaina et al, J. Auton Pharmacol, vol. 3, No. 2, pp. 115–26, Apr. 1993.

Matsubara et al., European Journal of Pharmacology, "UK–14304, R(–)-alpha–Methyl–Histamine and SMS 201–995 Block Plasma Protein Leakage within Dura Mater by Prejunctional Mechanisms", 224 (1992) 145–150.*

Sabbe et al, Anesthesiology 80:1057–1072, 1994.

Takano et al. The Journal of Pharmacology and Expperiental Therapeutics, V. 264, No. 2, pp. 327–335, 1992.

Takano et al. The Journal of Pharmacology and Experimental Therapeutics, v. 261, No. 2, pp. 764–772, 1992.

Yaksh et al. The Journal of Pharmacology and Experiental Therapeutics, v. 272, No. 1, pp. 207–214, 1995.

Kallgren, Buillier's Clinician Anaesthesiology, v. 9 No. 1, Mar. 1995, pp. 93–103.

Tanelian et al. Investigative Ophthalmology & Visual Science Feb. 1994, v. 35, No. 2, pp. 759–763.

Arrigo et al. Pharmological research. vol. 26, Supplemental 1, 1992.

Mittag, Annals of Ophthalmology, 15(3), 201–202, 1983.

Scrip Product Information, Scrip No. 1466, pp. 28, Nov. 1989.

* cited by examiner

METHODS FOR USING (2-IMIDAZOLIN-2-YLAMINO) QUINOXALINE DERIVATIVES

RELATED APPLICATIONS

This is a continuation-in-part of application Ser. No. 09/012,517, filed Jan. 23, 1998, now abandoned, which is a division of application Ser. No. 08/636,740, filed Apr. 19, 1996, now U.S. Pat. No. 5,756,503 which is a division of application Ser. No. 08/458,949, now U.S. Pat. No. 5,587,376 filed Jun. 2, 1995, which is a division of application Ser. No. 08/390,265, filed Feb. 15, 1995, now U.S. Pat. No. 5,561,132, which is a continuation of application Ser. No. 08/135,716, filed Oct. 13, 1993, now abandoned.

BACKGROUND OF THE INVENTION

The present invention relates to certain derivatives of quinoxaline. More particularly, the invention relates to methods of using such derivatives as therapeutic agents, for example, to effect reduction in peripheral pain, to anesthetize the central nervous system, to constrict one or more blood vessels, to treat ischemia, to decongest one or more nasal passages, and to effect reduction of one or more effects of an inflammatory disorder to increase renal fluid flow and to effect an alteration in the rate of fluid transport in the gastrointestinal tract.

Various quinoxaline derivatives have been suggested as therapeutic agents. For example, Danielewicz, et al U.S. Pat. No. 3,890,319 discloses compounds as regulators of the cardiovascular system and, in particular, in the treatment of hypertension, which have the following formula:

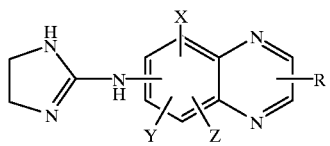

where the 2-imidazolin-2-ylamino group may be in any of the 5-, 6-, 7- or 8-position of the quinoxaline nucleus; X, Y and Z may be in any of the remaining 5-, 6-, 7- or 8-positions and may be selected from hydrogen, halogen, lower alkyl, lower alkoxy or trifluoromethyl; and R is an optional substituent in either the 2- or 3-position of the quinoxaline nucleus and may be hydrogen, lower alkyl or lower alkoxy. Gluchowski U.S. Pat. No. 5,021,416 discloses the use of similar quinoxaline derivatives to reduce or maintain the intraocular pressure in a mammalian eye. There is no suggestion in either of these patents that such compounds are useful in reducing peripheral pain, as central nervous system anesthetics, as vaso-constricting agents, to treat ischemia, as a nasal passage decongestant, to treat inflammatory disorders, to increase renal fluid flow or to alter the rate of fluid flow in the gastrointestinal tract.

SUMMARY OF THE INVENTION

New methods for treating mammals, preferably human beings, to provide a desired therapeutic effect have been discovered. By administering an effective amount of one or more of certain compounds to a mammal, a desired therapeutic effect is provided in the mammal. Such desired therapeutic effects include reduction in peripheral pain, that is reduction in acute peripheral and/or reduction in chronic peripheral pain, anesthetization of the central nervous system, constriction of one or more blood vessels, reduction in or prevention of at least one effect of ischemia, decongestion of one or more nasal passages, reduction in at least one effect of an inflammatory disorder, increase in renal fluid flow, and alteration, preferably decrease, in the rate of fluid transport in the gastrointestinal tract.

The quinoxaline derivatives useful in the present invention are those quinoxaline derivatives having the formula

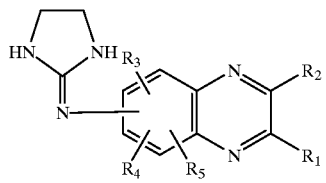

pharmaceutically acceptable acid addition salts thereof and mixtures thereof. $R_1$ and $R_2$ each is independently selected from the group consisting of H, alkyl radicals containing 1 to 4 carbon atoms and alkoxy radicals containing 1 to 4 carbon atoms. $R_2$ is preferably a methyl radical. The 2-imidazolin-2-ylamino group may be in any of the 5-, 6-, 7- and 8- positions, preferably in the 6- position, of the quinoxaline nucleus. $R_3$, $R_4$ and $R_5$ each is located in one of the remaining 5-, 6-, 7- or 8-positions of the quinoxaline nucleus and is independently selected from the group consisting of Cl, Br, H and alkyl radicals containing 1 to 3 carbon atoms. $R_3$ is preferably in the 5- position of the quinoxaline nucleus, and $R_4$ and $R_5$ are preferably both H. In a particularly useful embodiment $R_3$ is Br.

In one embodiment, $R_1$ is H and $R_2$ is selected from alkyl radicals containing 1 to 4 carbon atoms. $R_3$ may advantageously be in the 5- position of the quinoxaline nucleus and be selected from H and alkyl radicals containing 1 to 3 carbon atoms.

All stereoisomers, tautomers and mixtures thereof which comply with the constraints of one or more of the presently useful compounds are included within the scope of the present invention.

Pharmaceutically acceptable acid addition salts of the compounds of the invention are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

DETAILED DESCRIPTION OF THE INVENTION

The present invention involves methods for treating mammals to provide one or more desired therapeutic effects in the mammal. The present methods comprise administering an effective amount to provide the desired therapeutic effect or effects in a mammal of at least one compound, as described herein, to the mammal. Among the desired therapeutic effects are reduction in peripheral pain, that is reduction in acute peripheral pain and/or reduction in chronic peripheral pain, anesthetization of the central nervous system, constriction of one or more blood vessels, reduction in or prevention of at least one effect of ischemia, decongestion of one or more nasal passages, reduction in at least one effect of an inflammatory disorder, for example, such disorders characterized by progressive joint and/or tissue deterioration, increase in renal fluid flow, and alternation, preferably decrease, in the rate of fluid transport in the gastrointestinal tract. Thus, for example, the presently useful compounds may be effective as one or more of the following: a peripheral pain killing agent, a general anesthetic, a vasoconstricting agent, an agent for the treatment of ischemia, a nasal decongestant, an anti-inflammatory agent, a medication for use in the treatment or management of kidney disease, and an anti-diarrhea agent. One important feature of many of the present methods is that the desired therapeutic effect is achieved with reduced side effects, in particular with reduced effects on the blood pressure of the mammal to which the presently useful compound or compounds are administered.

Any suitable method of administering the presently useful compound or compounds to the mammal to be treated may be used. The particular method of administration chosen is preferably one which allows the presently useful compound or compounds to have the desired therapeutic effect in an effective manner, e.g., low medication concentration and low incidence of side effects. In many applications, the presently useful compound or compounds are administered to a mammal in a manner substantially similar to that used to administer alpha agonists, in particular alpha 2 agonists, to obtain the same or similar therapeutic effect or effects.

Administration of the presently useful compounds for use in the methods of this invention can include, but are not limited to, oral, parenteral, topical, intra-articular and other modes of systemic administration. The compounds are administered in a therapeutically effective amount either alone or in combination with a suitable pharmaceutically acceptable carrier or excipient.

Depending on the intended mode of administration, the presently useful compound or compounds may be incorporated in any pharmaceutically acceptable dosage form, such as for example, tablets, suppositories, pills, capsules, powders, liquids, suspensions, emulsions, aerosols or the like, preferably in unit dosage forms suitable for single administration of precise dosages, or sustained release dosage forms for continuous controlled administration. Preferably, the dosage form will include a pharmaceutically acceptable excipient and the presently useful compound or compounds and, in addition, may contain other medicinal agents, pharmaceutical agents, carriers, adjutants, etc.

For solid dosage forms, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. An example of a solid dosage form for carrying out the invention is a suppository containing propylene glycol as the carrier. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgement of the prescribing physician. The therapeutically effective dosage of the presently useful compound or compounds is preferably in the range of about 0.5 or about 1 to about 100 mg/kg/day.

The presently useful compounds are as described above. The presently useful compounds may be prepared in accordance with the procedures described in Danielewicz, et al U.S. Pat. No. 3,890,319 for the production of the quinoxaline derivatives therein. This patent is hereby S incorporated in its entirety by reference herein.

Briefly, the presently useful 2-imidazolin-2-ylamino quinoxaline derivatives may be prepared by (1) reaction of the appropriate amino-quinoxaline with thiophosgene to form the corresponding isothiocyanate; and (2) reacting this isothiocyanate with excess ethylene diamine to form the corresponding beta-aminoethyl-thioureidoquinoxaline, which is then cyclized to the corresponding derivative. Alternately, such derivatives can be prepared by (1) reacting the corresponding aminoquinoxaline with benzoyl isothiocyanate to form the corresponding N-benzoyl thioureido compound, followed by hydrolysis to the thioureido compound, or reaction of the aminoquinoxaline with ammonium thiocyanate to form the thioureido compound directly; (2) methylation to form the S-methyl derivative of the thioureido compound; and (3) reaction with ethylene diamine to form the derivative.

For derivatives in which the $R_3$ group is to be alkyl, the corresponding bromo derivative can be produced and than subjected to an alkylation reaction in which the bromo group is replaced by the desired alkyl group. This alkylation reaction is conveniently conducted using an alkylation agent, such as an alkyl metallic component, e.g., alkyl stannane, in the presence of a platinum group metal-containing catalyst. For example, if it is desired to substitute a methyl group for the bromo group, the bromo derivative is contacted with tetramethyl tin in the presence of a palladium-containing catalyst, e.g., $(Ph_3P)_2PdCl_2$, at conditions to effect the desired alkylation or substitution.

The following non-limiting examples illustrate certain aspects of the present invention.

EXAMPLE 1

Preparation of 6-(2-imidazolin-2-ylamino) quinoxaline 1,2,4-Triaminobenzene dihydrochloride To a suspension of 4-nitrophenylenediamine (Aldrich, 10 g, 65.3 mmol) in absolute ethanol (240 ml) was added 600 mg of 10% by weight palladium on charcoal catalyst. The container including the suspension was evacuated and filled with hydrogen three times and the suspension was hydrogenated at 18 psi until hydrogen uptake ceased. The reaction was slightly exothermic and one refill of hydrogen was required. The resulting light yellow solution, which darkens rapidly on contact with air, was filtered and concentrated to about 150 ml. Concentrated hydrochloric acid (12 ml) was added and the solid formed was filtered off. After drying in vacuo overnight, 12 g (a yield of 93%) of purple solid was obtained, m.p. 224–5° C. Using various analytical procedures, this solid was determined to be 1,2,4-triaminobenzene. dihydrochloride.

6-Aminoquinoxaline

Glyoxal sodium bisulfite adduct (Aldrich, 14.3g, 50 mmol) was added in small portions to a solution of 1,2,4-triaminobenzene dihydrochloride (9.8 g, 50 mmol) in 200 ml of 10% by weight sodium carbonate in water. The reaction mixture was heated to 100° C. for two hours and then cooled to 0° C. The crystals formed were filtered off and dried in vacuo to give a crude yield of 7.06 g (a yield of 97%) of brown crystals. Recrystallization from benzene gave 6.32 g (a yield of 87%) yellow crystals, m.p. 157–8° C. Using various analytical procedures, these yellow crystals were determined to be 6-aminoquinoxaline.

6-(2-imidazolin-2-ylamino) quinoxaline

6-Aminoquinoxaline (1.00 g, 7.5 mmol) was suspended in 15 ml of water and thiophosgene (0.64 ml, 8.4 mmol) was added in small portions with vigorous stirring. The starting material dissolved and after 2 hours the red color of the solution was discharged. The solid formed was removed by vacuum filtration and washed with water. The crude isothiocyanate thus obtained was used without further purification. A solution of the isothiocyanate in benzene (70 ml) was contacted with ethylenediamine (Aldrich, 2.71 g, 45 mmol) in 10 ml of benzene at 25° C. for 30 minutes. After stirring for an additional 30 minutes, the supernatant was poured off. The crude thiourea thus obtained was washed three (3) times with 10 ml dry ether and used directly for the next step. The crude product was dissolved in 30 ml of dry methanol and the dark green solution was heated at reflux for 15 hours until hydrogen sulfide gas was no longer evolved. The mixture was cooled to room temperature and concentrated in vacuo. The resulting dark green solid was chromatographed ($SiO_2$, 90/10 $CHCl_3/CH_3$ OH saturated with $NH_3$ (g) ) to yield a dark green solid which was recrystallized from $CH_3OH$ to yield 1.11 g of the title compound as a light green crystalline solid, mp 232–234° C. The yield was 70%. The compound was characterized by $^1H$ and $^{13}CNMR$, IR and mass spectral analysis.

EXAMPLE 2

Preparation of 5-bromo-6-(2-imidazolin-2-ylamino) quinoxaline

6-Amino-5-bromoquinoxaline hydrobromide

6-Aminoquinoxaline (2.08 g, 14.4 mmol) was dissolved in 11.5 ml glacial acetic acid. The solution was cooled in water while a solution of bromine (0.74 ml, 2.3 g, 14.4 mmol) in 1.5 ml glacial acetic acid was added slowly over 15 min. After stirring for an additional 30 min, the orange red solid formed was filtered off and washed thoroughly with dry ether. The solid was dried in vacuo overnight to yield 4.44 g crude product (a yield of 100%). The compound, 6-amino-5-bromoquinoxaline hydrobromide, had no definite melting point. A phase change (from fine powder to red crystals) was noticed at about 220° C. Decomposition was observed at about 245° C. It was used directly for the next step.

6-Amino-5-Bromoquinoxaline

The crude 6-amino-5-bromoquinoxaline from above was dissolved in water and saturated sodium bisulfite solution was added until the resulting solution tested negative with starch-iodide paper. The solution was then basified with 2N sodium hydroxide and extracted thoroughly with ethyl acetate. The organic extract was dried over magnesium sulfate and concentrated under reduced pressure to give the free base. The crude product was recrystallized from boiling benzene to give yellow crystals, m.p. 155–6° C. Using various analytical procedures, the yellow crystals were determined to be 6-amino-5-bromoquinoxaline. The yield was 82%.

5-Bromo-6-isothiocyanatoquinoxaline

The crude hydrobromide product previously noted (4.27g, 14.0 mmol) was dissolved in 60 ml of water and thiophosgene (Aldrich, 1.28 ml, 16.8 mmol) was added in small portions with vigorous stirring. After 2 hours, the red color of the solution was discharged. The solid formed was filtered off and washed thoroughly with water. After drying in vacuo at 25° C., 3.38 g (a yield of 90%) of brick red crystals was obtained, m.p. 157–8° C. A portion of this material was further purified by column chromatography to give white crystals, m.p. 157–8° C. Using various analytical procedures, these crystals were determined to be 5-bromo-6-isothiocyanatoquinoxaline.

5-Bromo-6(-N -(2-aminoethyl)thioureido) quinoxaline

A solution of the isothiocyanate (3.25 g, 12.2 mmol) in 145 ml benzene was added to a solution of ethylenediamine (Aldrich, 5.43 g, 90.0 mmol) in 18 ml benzene at 25° C. over 2 hours. After stirring for a further 30 min., the supernatant was poured off. The oil which remained was washed by swirling with dry ether three times and used directly for the next step.

A portion of this product was further purified by column chromatography ($SiO_2$, $CHCl_3$) for characterization. A white solid was recovered which decomposed at 175° C. with gas evolution (puffing). This white solid was determined to be 5-bromo-6(-N-2-(aminoethyl) thioureido) quinoxaline.

5-Bromo-6- (2-imidazolin-2-ylamino)quinoxaline

The crude product from above was dissolved in 100, ml dry methanol and the brown solution was refluxed for 19 hours until hydrogen sulfide gas was no longer evolved. The mixture was cooled to room temperature and concentrated to about 50 ml. The yellow solid was filtered off and dried in vacuo; weight 2.52 g (a yield of 70%), mp 242–4° C.

As the crude product was insoluble in most common organic solvents, initial purification was achieved by an acid-base extraction procedure. 23 g of the crude product was dissolved in 100 ml 0.5N hydrochloric acid. The turbid yellow solution was filtered to give a clear orange yellow solution which was extracted twice with ethyl acetate (2×10 ml). The aqueous phase was cooled to 0° C. and basified with 6N sodium hydroxide, keeping the temperature of the solution below 15° C. at all times. The yellow solid which precipitated was filtered off and washed thoroughly with water until the washings were neutral to pH paper. The solid was dried overnight in vacuo to give 1.97 g yellow solid, m.p. 249–50° C. The recovery was about 88%.

Further purification was achieved by recrystallization as described below. The partially purified product from above was dissolved in N, N-dimethylformamide (about 17 ml/g) at 100° C. with vigorous stirring. The solution was filtered hot and set aside to cool overnight. The bright yellow crystals were collected by filtration, m.p. 252–3° C. Recovery was from 65–77%. Using various analytical procedures, the bright yellow solid was determined to be 5-bromo-6-(2-imidazolin-2-ylamino) quinoxaline.

EXAMPLE 3

Preparation of 5-Methyl-6-(2-imidazolin-2-ylamino) quinoxaline

A sealable reaction tube was charged with 5-bromo-6-(2-imidazolin-2-ylamino) quinoxaline (104 mg., 0.36 mmol) (prepared as noted above), tetramethyl tin (214 mg., 1.2 mmol) and $(Ph_3P)_2PdCl_2$ (10 mg) and dry dimethylformamide (2 ml) in a reaction tube. The reaction mixture was purged with dry nitrogen gas. The tube was sealed and heated to 145° C. for 6 hours. The reaction mixture was cooled to room temperature and the solvent removed in vacuo. The dark brown residue was chromatographed ($SiO_2$; 5/1 $CHCl_3/CH_3OH$ saturated with $NH_3$ (g)) to yield 46.5 mg (53%) of the title compound as a light yellow solid. An analytical sample was prepared by recrystallization from $CHCl_3/CH_3OH$ and had a melting point of 183–186° C. The title compound was characterized by $^1H$ and $^{13}CNMR$ and mass spectral analysis.

EXAMPLE 4

Preparation of 2-Methyl-5-bromo-6-(2-imidazolin-2-ylamino)-quinoxaline

2-Methyl-6-nitroquinoxaline

A solution of pyruvic aldehyde (Aldrich, 40% solution in $H_2O$, 11.8 g, 65.3 mmol) was added dropwise to a solution of 4-nitro-1,2-phenylenediamine (Aldrich, 10 g, 65.3 mmol) in 150 ml of $H_2O$. The reaction mixture was heated to 80° C. for four hours. The reaction was cooled to room temperature, diluted with water and extracted with $CHCl_3$. The organic extracts were dried over $MgSO_4$ and evaporated to yield 10.7 g (a yield of 87%) of as a brick red solid. Using various analytical procedures, this solid was determined to be 2-methyl-6 nitroquinoxaline.

2-Methyl-6-Aminoquinoxaline

A thick-walled Parr hydrogenation flask was charged with 2-methyl-6-nitroquinoxaline (10.0 g, 52.9) and $CH_3OH$ (200 ml). The flask was flushed with a stream of nitrogen and 10% by weight palladium on charcoal (500 mg) was added. The flask was pressurized with hydrogen to 50 psi and maintained at this pressure for three (3) hours. The reaction mixture was filtered and washed through silicon dioxide and concentrated in vacuo to yield a tan solid. The crude material was chromatographed ($SiO_2$; 95/5 $CHCl_3/CH_3OH$ saturated with $NH_3$ (g)) and recrystallized from benzene to yield 7.4 g (a yield of 88%) of a tan solid. Using various analytical procedures, this tan solid was determined to be 2-methyl-6-aminoquinoxaline.

2-Methyl-5-bromo-6-(2-imidazolin-2-ylamino) quinoxaline

By a series of reaction steps analogous to the reaction steps described above in Example 2 to produce 5-bromo-6-(2-imidazolin-2-ylamino) quinoxaline, the title compound (mp: 260° C.) was prepared starting with 2-methyl-6-aminoquinoxaline in place of 6-aminoquinoxaline.

EXAMPLE 5

Preparation of 3-Methyl-5-bromo-6- (2-imidazolin-2 ylamino) -quinoxaline

3-Methyl-6-aminoquinoxaline

Pyruvic aldehyde (Aldrich, 892 mg, 4.95 mmol, 40% solution $H_2O$) was added dropwise to a stirred solution of 1, 2, 4-triaminobenzene hydrochloride (1.0 g, 4.95 mmol) dissolved in 10% aqueous $Na_2CO_3$ (15 ml). The mixture was heated at 100° C. for two hours before cooling to room temperature. The mixture was extracted with $CHCl_3$. The combined organic extracts were dried over $MgSO_4$ and concentrated in vacuo to yield a brown solid. The crude product was chromatographed ($SiO_2$, 95/5 $CHCl_3/CH_3OH$ saturated with $NH_3$ (g)) to yield 616 mg (a yield of 75%) of a yellow crystalline solid. An analytical sample was prepared by recrystallization from benzene, mp 170–173° C. Using various analytical procedures, the solid was determined to be 3-methyl-6-aminoquinoxaline.

3-Methyl-5-bromo-6- (2-imidazolin-2-ylamino) -quinoxaline

By a series of reaction steps analogous to the reaction steps described above in Example 2 to produce 5-bromo-6- (2 imidazolin-2-ylamino) quinoxaline, the title compound (mp>260° C.) was prepared starting with 3-methyl-6-aminoquinoxaline in place of 6-aminoquinoxaline.

EXAMPLE 6

Preparation of 2,3-dimethyl-5-bromo-6-(2-imidazolin-2-ylamino quinoxaline.

2,3-Dimethyl-6-aminoquinoxaline 2,3-butanedione (7.03 g, 81.7 mmol) was added to a solution of 1,2,4-triaminobenzene hydrochloride (16.5 g, 81.7 mmol) in aqueous 10% $Na_2CO_3$(200 ml). The reaction mixture was stirred at room temperature for 15 minutes during which time a yellow precipitate formed. The reaction mixture was stirred for an additional 30 minutes before collecting the solid by vacuum filtration. The solid was washed with water, dried in vacuo and chromatographed ($SiO_2$, ethylacetate) to yield 11.7 g (86%) of a tan solid, mp 185–186° C. Using various analytical procedures, this solid was determined to be 2,3-dimethyl-6-aminoquinoxaline.

2,3-dimethyl-5-bromo-6-(2-imidazolin-2ylamino)-quinoxaline

By a series of reaction steps analogous to the reaction steps described above in Example 2 to produce 5-bromo-6-(2-imidazolin-2-ylamino) quinoxaline, the title compound (mp 252–254° C.) was prepared starting with 2,3 -dimethyl-6-aminoquinoxaline in place of 6-aminoquinoxaline.

EXAMPLE 7

The final quinoxaline derivative produced in Example 2, that is 5-bromo-6-(2-imidazolin-2-ylamino)quinoxaline, was tested for central nervous system anesthetization activity as follows.

Two (2) animal models were utilized to determine the central nervous system anesthetization activity of the quinoxaline derivative produced in Example 2.

The first of these animal models is identified generally as the mouse hexobarbital sleep time test. Briefly, the compound in question (in a dosage range of between 10 and 500 micrograms/kg, i.v.) and the barbiturate hexobarbital (75 mg/kg, i.p) are coadministered to mice weighing 20 to 22 grams. The hexobarbital produces sleep which lasts for 10 to 14 minutes. Compounds which have central nervous system anesthetization activity potentiate the sleep time induced by hexobarbital. Sleep time is assessed as the time associated with the loss of the animal's reflex to right itself when placed on its back. The $ED_{15}$ is estimated from dose-response data as the effective dose which potentiates sleep time by 15 minutes. The second animal model used is identified generally as the rat activity test. Briefly, rats weighing 140 to 160 grams are placed into an environmentally isolated activity monitor five (5) minutes following administration of the compound in question (in the range of 1 to 1000 micrograms/kg, i.v.). Horizontal activity, measured in counts is determined for five (5) minutes. A dose-related loss of activity is obtained and fitted to an algorithm to estimate the $ID_{50}$ which is the dose which decreases activity by 50%.

The final quinoxaline derivative produced in Example 2 was tested using both of the above-noted animal models. For comparison purposes, clonidine and its hydrophilic analog, p-amino-clonidine, were also tested using these animal models.

Results of these tests are shown in the following table.

| Compound | $ED_{15}$ ($\mu$g/kg) Mouse Sleep-Time | $ID_{50}$ ($\mu$g/kg) Rat Activity |
| --- | --- | --- |
| Clonidine | 75 | 26 |
| p-Amino Clonidine | >500 | 302 |
| Example 2 | 116 | 77 |

These data demonstrate that the quinoxaline derivative produced in Example 2 has substantial central nervous system anesthetization activity. In particular, the Example 2 compound has a similar degree of such is activity as clonidine, which is known to exhibit significant anesthetization activity, and has substantially more of such activity than the hydrophilic analog of clonidine.

EXAMPLES 8 TO 13

The final quinoxaline derivative produced in each of Examples 1 to 6 is tested for activity as follows.
Rabbit Vas Deferens: Alpha 2 Adrenergic Receptors New Zealand white rabbits (2–3 kg) are killed by $CO_2$ inhalation and the vasa deferentia is removed. The prostatic ends of the vasa deferentia (2–3 cm lengths) are mounted between platinum ring electrodes in 9 ml organ baths and bathed in Krebs bicarbonate solution of the following composition (millimolar): NaCl 118.0; KCl 4.7; $CaCl_2$ 2.5; $MgSO_4$ 1.2; $KH_2P_4$ 1.2; glucose 11.0; $NaHCO_3$ 25.0; which solution is maintained at 35° C. and bubbled with 95% $O_2$ and 5% $CO_2$. The initial tension of the vas deferens is 0.5 g. The tissues are left to equilibrate for 30 minutes before stimulation is started. Vasa are then field stimulated (0.1 Hz, 2 ms pulse width at 90 mA) using a square wave stimulator (WPI A310 Accupulser with A385 stimulus) The contractions of the tissue are recorded isometrically using Grass FT03 force-displacement transducers and displayed on a Grass Model 7D polygraph. A cumulative concentration-response relationship is obtained for the quinoxaline derivative being tested with a 4 minute contact time at each concentration. Each of the final quinoxaline derivatives of Examples 1 to 5 is effective to reduce the response height. Therefore, such compounds may be properly classified as Alpha 2 agonists since they are also inhibited pharmacologically by treatment with rauwolscine.

EXAMPLES 14 TO 19

Each of the final quinoxaline derivatives produced in Examples 1 to 6 is tested for renal and blood pressure effects using the following method.

Young male (20–24 weeks old) Sprague-Dawley rats are used. Under ketamine (60 mg/kg b.wt. i.m.) and pentobarbital (i.p. to effect) anesthesia, medical grade plastic tubes are implanted into the abdominal aorta and vena cava via the femoral vessels. In addition, a Silastic-covered stainless steel cannula is sewn in the urinary bladder. After the surgery, the rats are housed individually and are allowed free access to food and water until the day of the experiment.

For about 7 to 10 days before surgery and during recovery, the rats are accustomed to a restraining cage by placement in the cage for 2 to 3 hours every 2nd and 3rd day. The cage is designed for renal clearance studies (a model G Restrainer sold by Braintree Scientific, Inc., Braintree, Mass.). The animals' adjustment to the cage is judged by the stability of blood pressure and heart rate.

For an experiment, a rat is placed in the restraining cage, and the arterial line is connected to a Statham pressure transducer and a Beckman Dynograph R61 to monitor the mean arterial blood pressure, hereinafter referred to as MAP. The venous line is connected to an infusion pump system for infusion of replacement fluid. The quinoxaline derivative is administered intraduodenally by cannula. The bladder cannula was extended with a silastic tube to facilitate collection of urine in preweighed tubes. The volume of urine is measured gravimetrically. Body weight is recorded before and after the experiment.

Throughout the experiments, 0.9% NaCl containing 10% polyfructosan (Inutest) and 1% sodium PAH is infused at a rate of 20 microliters/min. An equilibration period of 60 minutes is followed by two consecutive 30 minute control clearance periods. Then, the quinoxaline derivative is administered for 90 minutes. Urine collection is resumed 10 minutes after the start of quinoxaline derivative administration. By this time the washout of the bladder cannula dead space (approximately 200 microliters) is completed. Three additional clearance measurements are made. Blood samples (150 microliters) are collected at the midpoint of urine collections. Plasma is separated and saved for analyses, and the cells are resuspended in saline and returned to the animals. Water and sodium loss is carefully replaced i.v. by a variable speed infusion pump.

Results of these tests indicate that the present quinoxaline derivatives produce renal effects, e.g., increased renal fluid flow. The effect on blood pressure of such derivatives is limited relative to such renal effects.

EXAMPLES 20 TO 25

Each of the final quinoxaline derivative produced in Examples 1 to 6 is tested for anti-diarrheal effects and blood pressure effects using the following method.

Cecectomies are performed in unfasted rats in a conventional manner. The cecectomized rats are put into individual wire-bottomed cages placed over sheets of clean paper, and deprived of food and water for the duration of the assay. The MAP is monitored, as described in Examples 17 to 20, throughout the assay. Rats are given a 2 hour acclimatization period prior to the start of the assay in order to eliminate sporadic episodes of anxiety-induced defecation. During this period they are observed also for consistent occurrences of pelleted feces; an animal producing other than a pelleted stool is disqualified from the study.

Diarrhea is induced with oral administration of 16,16-dimethyl prostaglandin $E_2$ (dmPGE$_2$) in 3.5% EtOH. The quinoxaline derivative is administered by gavage after the onset of diarrheal episodes. The cage papers are removed and examined at 30 minute intervals for dmPGE$_2$-induced diarrhea. Fecal output is recorded at each interval and fecal consistency is assigned a numerical score in each experimental group as follows: 1=normal pelleted stool; 2=soft-formed stools; 3=water stool and/or diarrhea. The fecal output index (FOI) is defined as the summation of the number of defecation episodes and their ranked consistency score within an observation period.

Results of these tests indicate that each of the final quinoxaline derivatives produced in Examples 1 to 5 provides substantial anti-diarrheal effects. Further, such anti-diarrheal effects are produced with relatively limited effects on blood pressure.

While this invention has been described with respect to various specific examples and embodiments, it is to be understood that the invention is not limited thereto and that it can be variously practiced within the scope of the following claims.

What is claims is:

1. A method of treating a mammal comprising administering to a mammal an effective amount to provide a desired therapeutic effect in said mammal of a compound selected from the group consisting of those having the formula

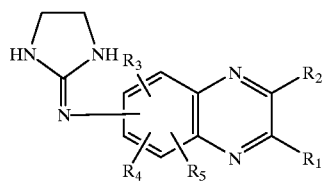

and pharmaceutically acceptable acid addition salts thereof and mixtures thereof, wherein $R_1$ and $R_2$ each is independently selected from the group consisting of H, alkyl radicals containing 1 to 4 carbon atoms and alkoxy radicals containing 1 to 4 carbon atoms, the 2-imidazolin-2-ylamino group may be in any of the 5-, 6-, 7- or 8-positions of the quinoxaline nucleus, and $R_3$, $R_4$ and $R_5$ each is located in one of the remaining 5-, 6-, 7- and 8-positions of the quinoxaline nucleus and is independently selected from the group consisting of Cl, Br, H and alkyl radicals containing 1 to 3 carbon atoms, said desired therapeutic effect being reduction in chronic peripheral pain.

2. The method of claim 1 wherein the 2-imidazolin-2-ylamino group is in the 6-position of the quinoxaline nucleus, $R_3$ is in the 5-position of the quinoxaline nucleus and is selected from the group consisting of Cl, Br and alkyl radicals containing 1 to 3 carbon atoms, and $R_4$ and $R_5$ are both H.

3. The method of claim 2 wherein $R_2$ is a methyl radical.

4. The method of claim 3 wherein $R_3$ is Br.

5. The method of claim 2 wherein $R_3$ is Br.

6. The method of claim 1 wherein $R_2$ is a methyl radical.

7. The method of claim 1 wherein $R_1$ is H and $R_2$ is selected from the group consisting of alkyl radicals containing 1 to 4 carbon atoms and alkoxy radicals containing 1 to 4 carbon atoms.

8. The method of claim 1 wherein said formula is

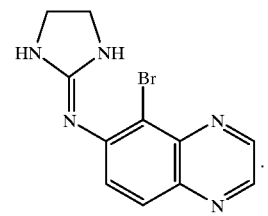

9. The method of claim 1 wherein $R_3$ is in the 5-position of the quinoxaline nucleus and is selected from the group consisting of H and alkyl radicals containing 1 to 3 carbon atoms.

10. The method of claim 9 wherein the 2-imidazolin-2-ylamino group is in the 6- position of the quinoxaline nucleus, and $R_4$ and $R_5$ are both H.

11. The method of claim 10 wherein both $R_3$ is selected from the group consisting of H and methyl radical.

12. The method of claim 9 wherein both $R_1$ and $R_2$ are H.

13. The method of claim 12 wherein $R_3$ is selected from the group consisting of H and methyl radical.

14. The method of claim 9 wherein $R_3$ is selected from the group consisting of H and methyl radical.

15. The method of claim 1 wherein both $R_1$ and $R_2$ are H.

16. The method of claim 1 wherein said formula is:

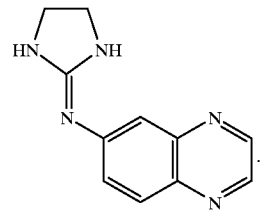

17. The method of claim 1 wherein said formula is:

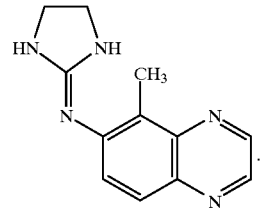

* * * * *

UNITED STATES PATENT AND TRADEMARK OFFICE
CERTIFICATE OF CORRECTION

PATENT NO.    : 6,323,204 B1
DATED         : November 27, 2001
INVENTOR(S)   : Burke et al.

It is certified that error appears in the above-identified patent and that said Letters Patent is hereby corrected as shown below:

Column 4,
Line 26, "hereby S incorporated" should read -- hereby incorporated --.

Column 5,
Line 11, "triaminobenzene. dihydrochloride" should read
-- triaminobenzene dihydrochloride --.

Column 6,
Line 52, "100, ml" should read -- 100 ml --.

Column 8,
Line 2, "mp:" should read -- mp. --.
Line 51, "2ylamino)" should read -- 2-ylamino) --.

Column 12,
Line 28, "wherein both $R_3$" should read -- wherein $R_3$ --.

Signed and Sealed this

Twenty-third Day of December, 2003

JAMES E. ROGAN
*Director of the United States Patent and Trademark Office*